United States Patent
Dalton

(10) Patent No.: US 6,945,974 B2
(45) Date of Patent: Sep. 20, 2005

(54) SPINAL STABILIZATION IMPLANT AND METHOD OF APPLICATION

(75) Inventor: Brian E. Dalton, Erie, PA (US)

(73) Assignee: Aesculap Inc., Center Valley, PA (US)

( * ) Notice: Subject to any disclaimer, the term of this patent is extended or adjusted under 35 U.S.C. 154(b) by 0 days.

(21) Appl. No.: 10/615,196

(22) Filed: Jul. 7, 2003

(65) Prior Publication Data

US 2005/0010217 A1 Jan. 13, 2005

(51) Int. Cl.$^7$ ............................................. A61B 17/58
(52) U.S. Cl. .......................................... 606/70; 61/69
(58) Field of Search ....................... 606/60, 61, 69–73

(56) References Cited

U.S. PATENT DOCUMENTS

| | | |
|---|---|---|
| 4,463,753 A | 8/1984 | Gustilo |
| 4,484,570 A | 11/1984 | Sutter et al. |
| 5,129,899 A | 7/1992 | Small et al. |
| 5,147,363 A | 9/1992 | Härle |
| 5,486,176 A | 1/1996 | Hildebrand et al. |
| 5,520,690 A | 5/1996 | Errico et al. |
| 5,531,746 A | 7/1996 | Errico et al. |
| 5,540,690 A * | 7/1996 | Miller et al. .................. 606/61 |
| 5,607,426 A | 3/1997 | Ralph et al. |
| 5,620,443 A | 4/1997 | Gertzbein et al. |
| 5,669,911 A | 9/1997 | Errico et al. |
| 5,735,853 A | 4/1998 | Olerud |
| 5,749,916 A | 5/1998 | Richelsoph |
| 5,797,911 A | 8/1998 | Sherman et al. |
| 5,800,433 A | 9/1998 | Benzel et al. |
| 5,863,293 A | 1/1999 | Richelsoph |
| 5,876,402 A | 3/1999 | Errico et al. |
| 5,879,350 A | 3/1999 | Sherman et al. |
| 5,885,286 A | 3/1999 | Sherman et al. |
| 5,954,635 A | 9/1999 | Foley et al. |
| 5,954,722 A | 9/1999 | Bono |
| 5,964,760 A | 10/1999 | Richelsoph |
| 5,976,187 A | 11/1999 | Richelsoph |
| 6,022,350 A | 2/2000 | Ganem |
| 6,030,389 A | 2/2000 | Wagner et al. |
| 6,033,406 A | 3/2000 | Mathews |
| 6,053,917 A | 4/2000 | Sherman et al. |
| 6,074,391 A | 6/2000 | Metz-Stavenhagen et al. |
| 6,083,225 A | 7/2000 | Winslow et al. |
| 6,096,038 A | 8/2000 | Michelson |
| 6,132,432 A | 10/2000 | Richelsoph |

(Continued)

*Primary Examiner*—Glenn K. Dawson
*Assistant Examiner*—D. Jacob Davis
(74) *Attorney, Agent, or Firm*—RatnerPrestia

(57) ABSTRACT

Vertebra bodies in the human spine are stabilized through the use of minimally invasive surgery for the implantation of an elongate implant plate assembly having spaced first and second screw receiving socket elements which are configured for respective attachment to first and second spaced vertebra with the aid of bone fixation screws and these elements are slidably received with respect to each other for adjustably changing the distance between the screw receiving socket elements. A lock assembly is also provided for selectively locking the first and second screw receiving elements from further relative sliding. An elongate insertion tool is releaseably secured to the proximal end of this plate assembly whereby the tool and the elongate plate assembly extend together end to end in their direction of elongation when secured together, and the insertion tool is configured for manipulating the plate assembly as a whole and for remotely manipulating the screw receiving socket elements for adjusting the distance therebetween. The plate assembly is inserted through an incision and manipulated and advanced with the insertion tool to provide minimally invasive insertion, and after fixation of the implant assembly with bone fixation screws is further utilized to adjust the degree of compression on the vertebra, and thereafter the implant is locked in position to prevent further relative movement between the screw receiving elements of the plate assembly.

10 Claims, 8 Drawing Sheets

U.S. PATENT DOCUMENTS

| | | | |
|---|---|---|---|
| 6,146,386 A | 11/2000 | Blackman et al. | |
| 6,152,871 A | 11/2000 | Foley et al. | |
| 6,159,179 A | 12/2000 | Simonson | |
| 6,162,170 A | 12/2000 | Foley et al. | |
| 6,171,311 B1 | 1/2001 | Richelsoph | |
| 6,197,033 B1 | 3/2001 | Haid, Jr. et al. | |
| 6,200,322 B1 | 3/2001 | Branch et al. | |
| 6,206,822 B1 | 3/2001 | Foley et al. | |
| 6,217,509 B1 | 4/2001 | Foley et al. | |
| 6,235,033 B1 | 5/2001 | Brace et al. | |
| 6,261,291 B1 | 7/2001 | Talaber et al. | |
| 6,280,442 B1 | 8/2001 | Barker et al. | |
| 6,280,445 B1 | 8/2001 | Morrison et al. | |
| 6,287,311 B1 | 9/2001 | Sherman et al. | |
| 6,290,703 B1 * | 9/2001 | Ganem | 606/73 |
| 6,299,616 B1 | 10/2001 | Beger | |
| 6,328,738 B1 | 12/2001 | Suddaby | |
| 6,328,740 B1 | 12/2001 | Richelsoph | |
| 6,328,741 B1 | 12/2001 | Richelsoph | |
| 6,331,179 B1 | 12/2001 | Freid et al. | |
| RE37,665 E | 4/2002 | Ralph et al. | |
| 6,402,752 B2 | 6/2002 | Schäffler-Wachter et al. | |
| 6,402,756 B1 | 6/2002 | Ralph et al. | |
| 6,428,542 B1 | 8/2002 | Michelson | |
| 6,451,021 B1 | 9/2002 | Ralph et al. | |
| 6,514,260 B1 | 2/2003 | Zdeblick et al. | |
| 6,520,907 B1 | 2/2003 | Foley et al. | |
| 6,527,776 B1 | 3/2003 | Michelson | |
| 6,530,929 B1 | 3/2003 | Justis et al. | |
| 6,533,786 B1 | 3/2003 | Needham et al. | |
| 6,562,046 B2 | 5/2003 | Sasso | |
| 6,565,565 B1 | 5/2003 | Yuan et al. | |
| 6,575,899 B1 | 6/2003 | Foley et al. | |
| 6,575,975 B2 | 6/2003 | Brace et al. | |
| 6,599,290 B2 | 7/2003 | Bailey et al. | |
| 6,602,255 B1 | 8/2003 | Campbell et al. | |
| 6,623,485 B2 | 9/2003 | Doubler et al. | |
| 6,645,207 B2 | 11/2003 | Dixon et al. | |
| 6,663,616 B1 | 12/2003 | Roth et al. | |
| 6,682,534 B2 | 1/2004 | Patel et al. | |
| 6,695,772 B1 | 2/2004 | Bon et al. | |
| 6,695,846 B2 | 2/2004 | Richelsoph et al. | |
| 6,712,818 B1 | 3/2004 | Michelson | |
| 6,712,819 B2 | 3/2004 | Zucherman et al. | |
| 6,780,185 B2 | 8/2004 | Frei et al. | |
| 6,780,186 B2 | 8/2004 | Errico et al. | |
| 2001/0034521 A1 | 10/2001 | Bailey et al. | |
| 2001/0037111 A1 * | 11/2001 | Dixon et al. | 606/61 |
| 2002/0161368 A1 | 10/2002 | Foley et al. | |
| 2002/0183754 A1 | 12/2002 | Michelson | |
| 2003/0045875 A1 * | 3/2003 | Bertranou et al. | 606/61 |
| 2003/0060826 A1 | 3/2003 | Foley et al. | |
| 2003/0073996 A1 | 4/2003 | Doubler et al. | |
| 2003/0149431 A1 | 8/2003 | Varieur | |
| 2003/0208203 A1 | 11/2003 | Lim et al. | |
| 2003/0216735 A1 | 11/2003 | Altarac et al. | |
| 2004/0039384 A1 | 2/2004 | Boehm, Jr. et al. | |
| 2004/0127897 A1 | 7/2004 | Freid et al. | |
| 2004/0133207 A1 | 7/2004 | Abodou | |

* cited by examiner

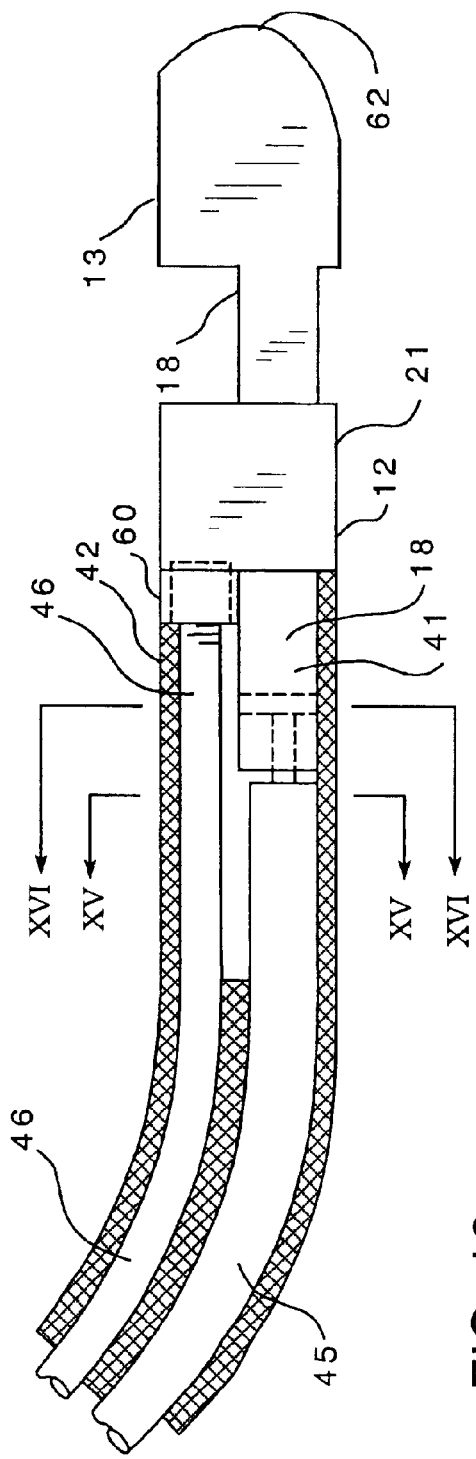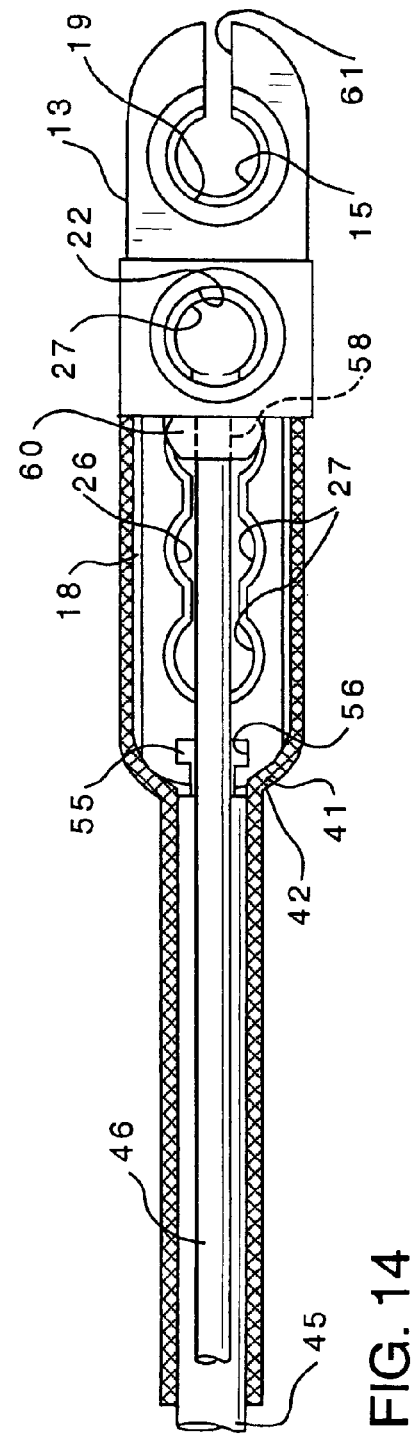
FIG. 13
FIG. 14

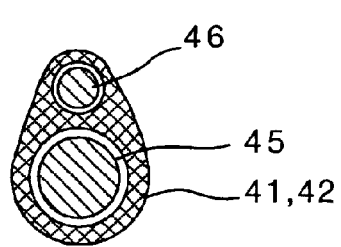
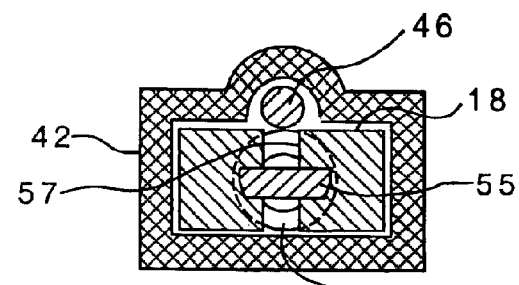
FIG. 15     FIG. 16
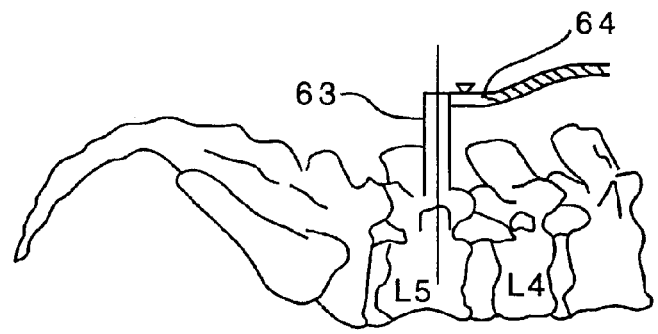
FIG. 17
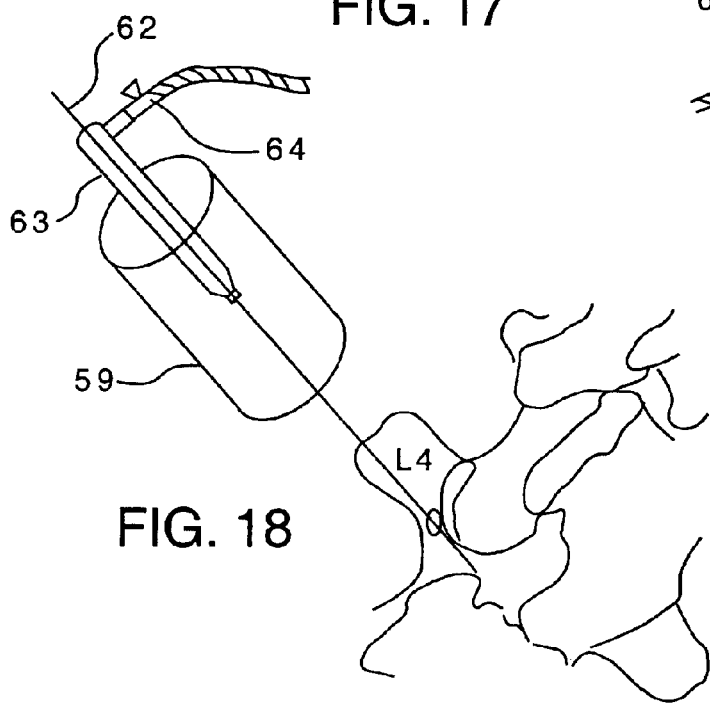
FIG. 18
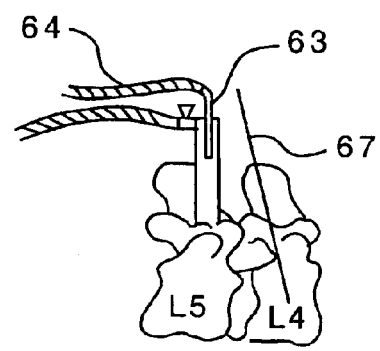
FIG. 19

SPINAL STABILIZATION IMPLANT AND METHOD OF APPLICATION

FIELD OF THE INVENTION

The present invention relates generally to fixation systems for osteosynthesis of the spine, and more particularly, it pertains to a spinal implant system and a surgical procedure for inserting and applying the implant.

BACKGROUND OF THE INVENTION

Spinal surgery on the lumbar and thoracic spines have classically been open operations, meaning that the instrumentation used is placed through an incision that exposes all of the spine to be instrumented, as well as a portion of spine above and below the area to be instrumented due to the need for proper visualization. This extensive exposure disrupts a considerable amount of tissue, particularly the lumbar paraspinal musculature which needs to be stripped off the vertebra bones for exposure. This stripping leads to muscle damage directly caused by either electrical cautery or manual cutting or indirectly by interruption of vascular supply to the muscle due to coagulation or cutting of vessels, and caused also by embarrassment of the vascular supply during the course of surgery due to compression by retractors on the muscle which are required to maintain exposure. In addition, spinal implants can impact upon the facet joints of the spine, particularly the upper most pair of pedicle screws, which can cause pain or dysfunction of the involved joint. This is due in part to the fact that the pedicle screw systems are designed to give stability without being made to respect normal anatomy. In other words, the spine is forced to fit the metal, instead of fitting the metal to the spine.

The present day surgical approach therefore has added to patient morbidity due to the extent of the surgical exposure, tissue damage done primarily to the posterior longitudinal musculature of the spine during the exposure, blood loss and risk of infection. Large open operations also tend to be the cause of significant postoperative pain and disability. Accordingly, these issues lead to longer hospital stays, higher postoperative complications, such as phlebitis and pneumonia brought on by immobility, and greater consumption of postoperative medications with their resultant side affects. In addition, the paraspinal muscle tissue damage has been implicated in the genesis of postoperative lumbar mechanical dysfunction and stiffness leading to postoperative pain syndromes or failed back syndrome. Also, interference by metal implants of the normal function of the rostral facet joints has been implicated in the early degeneration of these joints, as well as pain and disability, all which could lead to other more involved surgeries.

It is a principal object of the present invention to provide a system, including the spinal implant and a delivery system for applying the implant which allows for minimally invasive placement of the spinal implant, thereby reducing the undesired aforedescribed disadvantages of the prior art surgical procedures.

SUMMARY OF THE INVENTION

The present invention provides a system of spinal instrumentation used as an aid in bony fusion and stabilization of the spine in conjunction with minimally invasive spinal surgery not heretofore envisioned. The apparatus or system of the present invention is unique in that it permits placement, manipulation within the body and expansion and contraction of the implant to exert various pressures or forces on the spinal segment, but with minimally invasive techniques. This is made possible by the novel spinal implant assembly of the present invention, as well as the implant assembly insertion tool and system of the present invention which permits such minimally invasive techniques.

An implant plate assembly is provided as part of the system of the present invention and is comprised of a first screw receiving socket element at a distal end thereof and is configured with a screw shank passage and a screw head seat for attachment to vertebra with a aid of a bone fixation screw, and an elongate arm extends proximally from this first socket and has an elongate through slot therealong. A second screw receiving socket element is provided and is also configured with a screw shank passage and a screw head seat. This second screw receiving socket element is slidably received over the arm with its passage aligned over the slot for receiving the shank of a fixation screw therethrough for attachment to an underlying vertebra. The second socket element and the underlying slot are configured and dimensioned whereby portions of a screw head of a fixation screw seated in this socket element protrude through the second socket element passage and engage edges of the slot for thereby clamping the second socket element to the arm when the screw is fully secured in an underlying vertebra. To ensure locking, the edges of the slot are preferably provided with a series of adjacent screw head seat depressions for selectively seating portions of the screw head, thereby insuring that no more relative movement between the two screw receiving socket elements occurs.

Cap buttress nuts are threadably received in each of the socket elements over the screw heads for engaging and covering the screw heads. The nuts are also provided with bottom protuberances for engaging the screw heads as a lock to prevent accidental dislodgement or backing off of the screws.

The system of the present invention further envisions the use of an insertion tool or gun for inserting the implant plate assembly of the present invention as just described or for inserting an implant plate assembly of different design. When using the insertion tool of the present invention, the distal end of the plate assembly is provided with a leading transverse edge which is tapered in order to provide a self-cutting action during insertion by minimally invasive techniques. In addition, the plate assembly may be longitudinally curved to mate a specific lordotic curve of the spine.

The elongate insertion tool of present invention is releaseably secureable to the proximal end of the plate assembly whereby the tool and elongate assembly is secured together, extend together end to end in their direction of elongation. The insertion tool is configured for manipulating the plate assembly as a whole unit and for also remotely manipulating the screw receiving elements of the plate assembly for adjusting the distance between these elements. To aid in guiding the plate assembly upon insertion, guide wires may be employed and in this event an open ended guide wire capture slot is provided in the distal end of the plate assembly which communicates with the screw shank passage in the first screw receiving element of the plate assembly.

With the insertion tool and plate assembly combination of the present invention, the minimally invasive surgical procedure of the present invention for inserting the implant may be accomplished in order to stabilize adjacent vertebra bodies in the human spine. The procedure of the present invention requires securing the insertion tool to the proximal end of the plate assembly for manipulation of the plate assembly by the insertion tool. An incision is made in the body adjacent what is designated as a second vertebra for inserting the implant plate assembly and the implant plate assembly is inserted into the incision by manipulating the insertion tool, distal end first, and positioned whereby the second screw receiving socket of the plate assembly is positioned as required over the second vertebra by further manipulation of the insertion tool. Then the proximal end of the plate assembly is partially secured to this second vertebra with a bone fixation screw received in the second screw receiving socket of the plate assembly. Thereafter the distal end of the plate assembly is extended relative to its proximal end, thereby positioning the first screw receiving socket over an adjacent first vertebra by remote manipulation with the insertion tool. The distal end of the plate assembly is then secured to this first vertebra with a bone fixation screw received in the first screw receiving socket of the plate assembly.

Thereafter, the distance between the first and second socket elements of the plate assembly are adjusted to a desired degree by remote manipulation of the socket elements of the plate assembly with the use of the insertion tool for thereby adjusting the distance between the two secured vertebra. Then the proximal second screw which was previously only partially secured is fully secured. At this point, the two socket elements of the plate assembly are locked together from further relative movement either by use of prior art techniques or by full securement of the proximal second screw in accordance with the teachings of the novel plate assembly of the present invention as previously described. The minimally invasive implantation having been completed, the insertion tool is then detached from the implant plate assembly and removed from the field. This described surgical procedure of the present invention may be further aided by guiding the manipulations of the implant plate assembly relative to the vertebra by using fluoroscopy. In addition, guide wires may also be utilized as previously indicated by prepenetrating the first and second vertebra for thereby providing guide channels for the screws. The guide wires are positioned in the guide channels prior to the steps of securing the plate assembly by inserting and securing the plate assembly with self tapping cannulated pedicle screws which are received over and guided by these guide wires. After securement, the guide wires are removed.

The surgical procedure of the present invention may be further enhanced by using an open ended guide slot in the distal end of the plate assembly as previously indicated wherein the distal end of the assembly includes a guide slot in the leading edge which provides access to the distal screw securement passage in the first screw receiving socket element of the plate assembly. Then with the aid of the insertion tool, the plate assembly is guided whereby the distal end of the assembly captures a pre-inserted distal guide wire in the slot while extending the distal end of the plate assembly until the distal passage of the first socket element is centered over the distal guide wire.

BRIEF DESCRIPTION OF DRAWINGS

Other objects and advantages appear hereinafter in the following description and claims. The accompanying drawings show, for purpose of exemplification, without limiting the invention or the appended claims, certain practical embodiments of the present invention wherein:

FIG. 13 is a view in side elevation, with major portions thereof shown in vertical mid cross section to expose the interior, of the distal end of the elongate insertion tool of FIG. 12;

FIG. 14 is a top or plan view of the distal portion of the insertion tool shown in FIG. 13 with exterior portions thereof shown in horizontal mid cross section to expose the interior thereof;

FIG. 15 is an end view in vertical cross section of the distal portion of the elongate insertion tool shown in FIG. 13 as seen along section line XV—XV;

FIG. 16 is an end view in vertical cross section of the elongate insertion tool shown in FIG. 13 as seen along section line XVI—XVI;

FIGS. 17, 18, 19, 20, 21, 22 and 23 are schematic illustrations, not to scale, sequentially illustrating a first surgical technique of the present invention for inserting and applying to the human spine a plate assembly of the type illustrated in FIG. 10 with the elongate insertion tool illustrated in FIGS. 13 through 16.

DETAILED DESCRIPTION OF THE PREFERRED EMBODIMENTS

Figure 1:
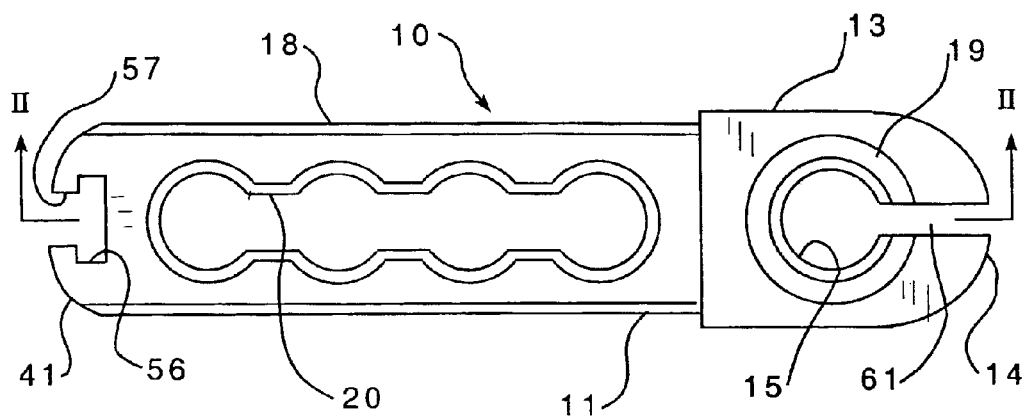
FIG. 1 is a plan view showing a first portion of the implant plate assembly of the present invention incorporating a first screw receiving socket element.
Figure 2:
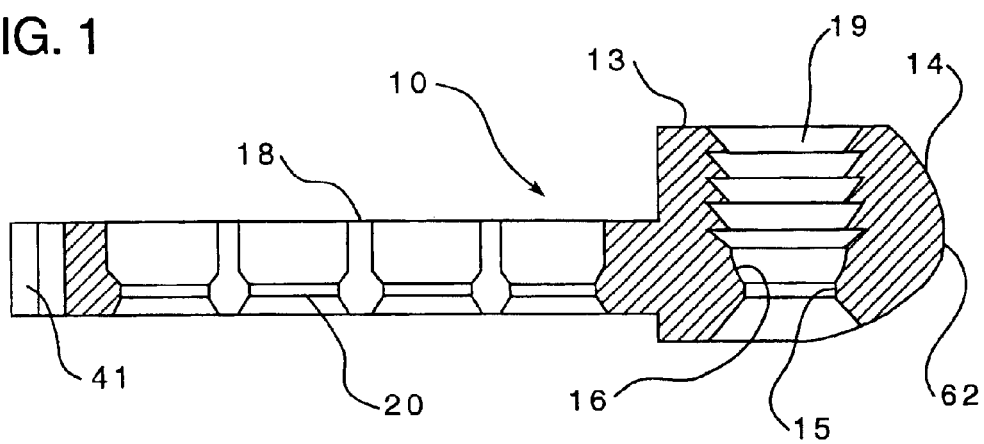
FIG. 2 is a view in front elevation and in vertical mid cross section of the implant plate assembly shown in FIG. 1 as seen along section line II—II.
Figure 3:
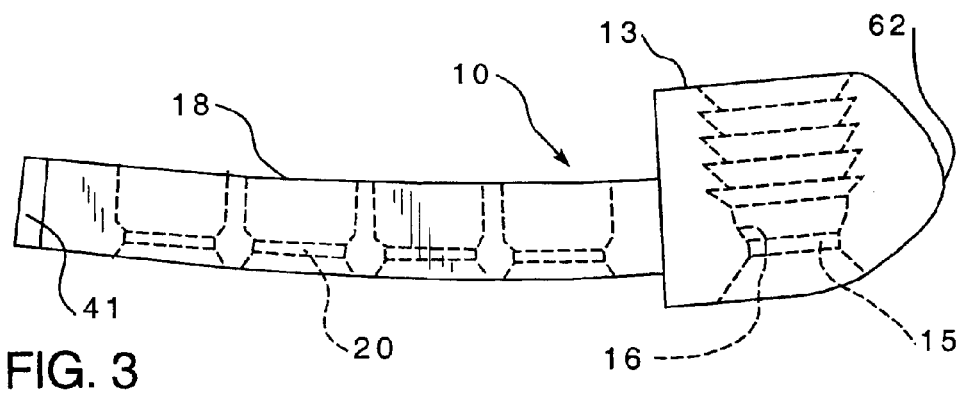
FIG. 3 is a view in front elevation of a modified version of the implant plate assembly shown in FIG. 1 with a downward lordotic curve.
Figure 4:
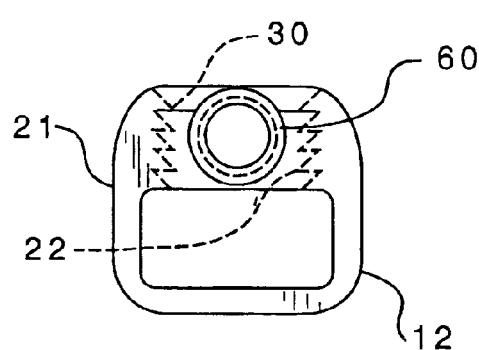
FIG. 4 is an end view of a second portion of the implant plate assembly of the present invention which incorporates a second screw receiving socket element to be combined with the first portion illustrated in FIG. 1.
Figure 5:
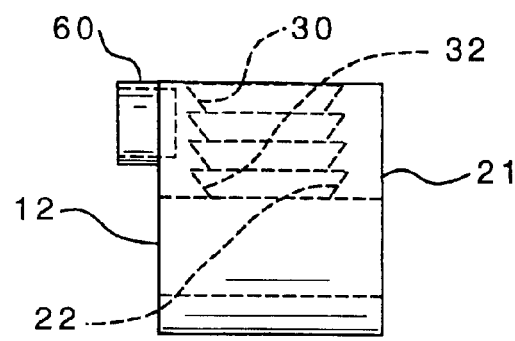
FIG. 5 is a right side view in front elevation of the second screw receiving socket element shown in FIG. 4.
Figure 6:
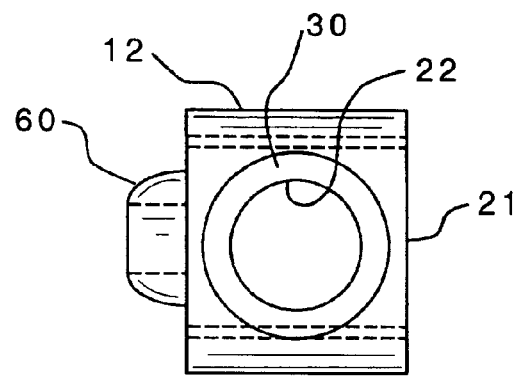
FIG. 6 is a plan or top view of the second screw receiving socket element shown in FIG. 5.

Referring first to FIGS. 1 through 11, the implant plate assembly 10 of the present invention for stabilization of the spine is comprised of two separate portions, a first portion 11 as separately illustrated in FIGS. 1 through 3, and a second portion 12 illustrated in FIGS. 4 through 6. These two portions of the assembly are illustrated in combined form in FIGS. 10 and 11.

The first portion 11 includes a first receiving socket element 13 at the distal end 14 of assembly 10. This first screw receiving socket element 13 is configured with a screw shank passage 15 and a screw head seat 16 for attachment of element 13 to a vertebra with the aid of a bone fixation screw 17 illustrated in FIG. 11.

Figure 7:
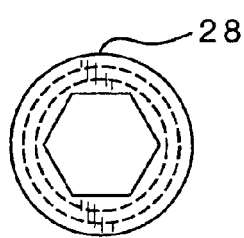
FIG. 7 is a top view of a cap buttress nut for threadably closing off the screw receiving socket elements illustrated in FIGS. 1 through 6.
Figure 8:
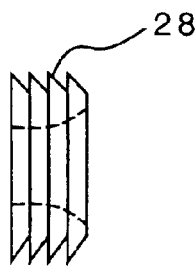
FIG. 8 is a view in side elevation of the cap buttress nut shown in FIG. 7.
Figure 9:
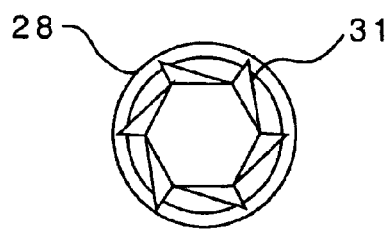
FIG. 9 is a bottom view of the cap buttress nut shown in FIGS. 7 and 8.
Figure 10:
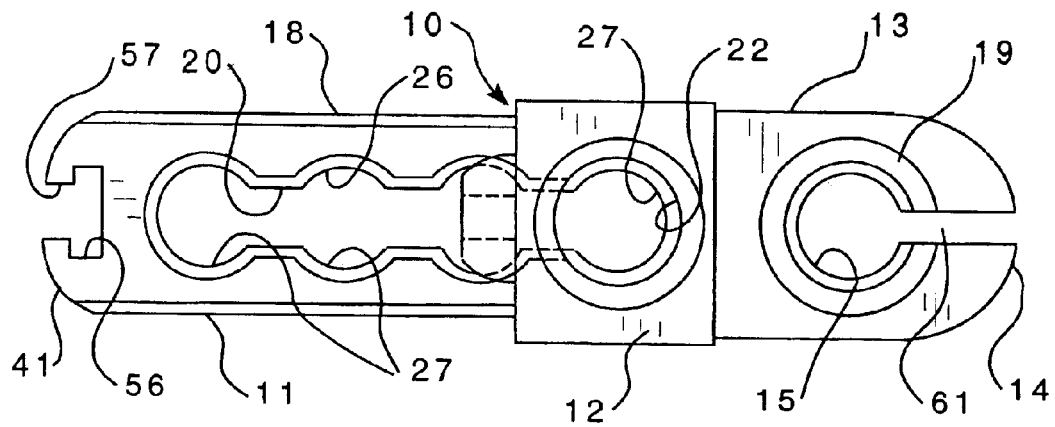
FIG. 10 is a plan view of the implant plate assembly of the present invention showing in combination the first portion illustrated in FIGS. 1 and 2 as combined with the second portion illustrated in FIGS. 4, 5 and 6.
Figure 11:
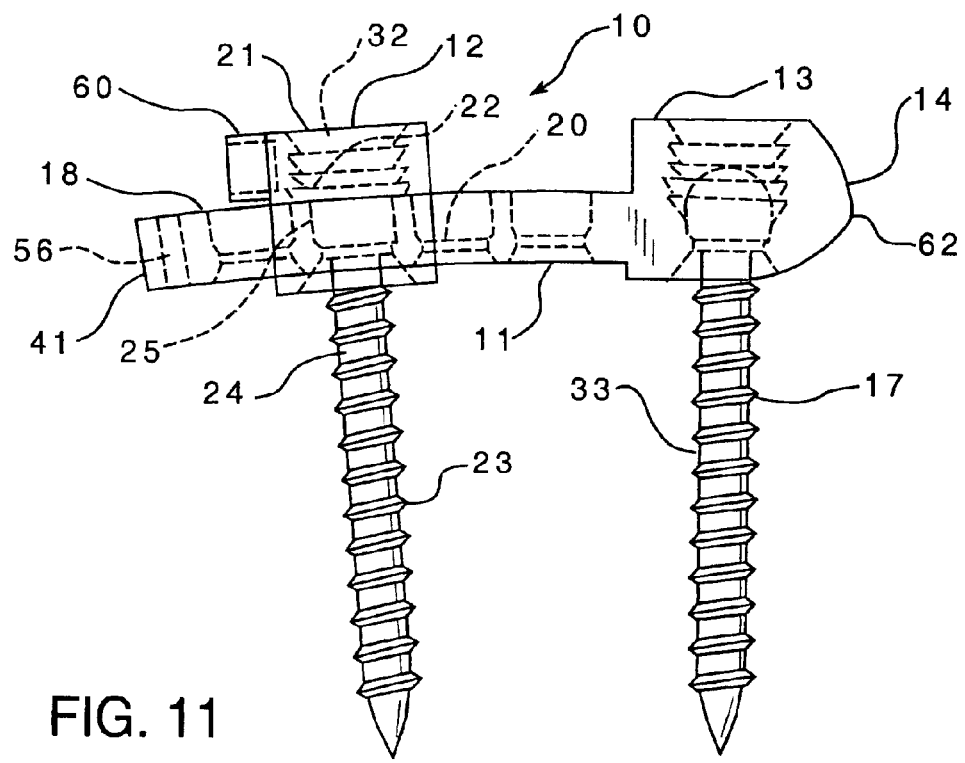
FIG. 11 is a view in front elevation of the complete implant assembly of the type illustrated in FIG. 10 as shown in further combination with bone fixation screws and an upward lordotic curve.
Figure 12:
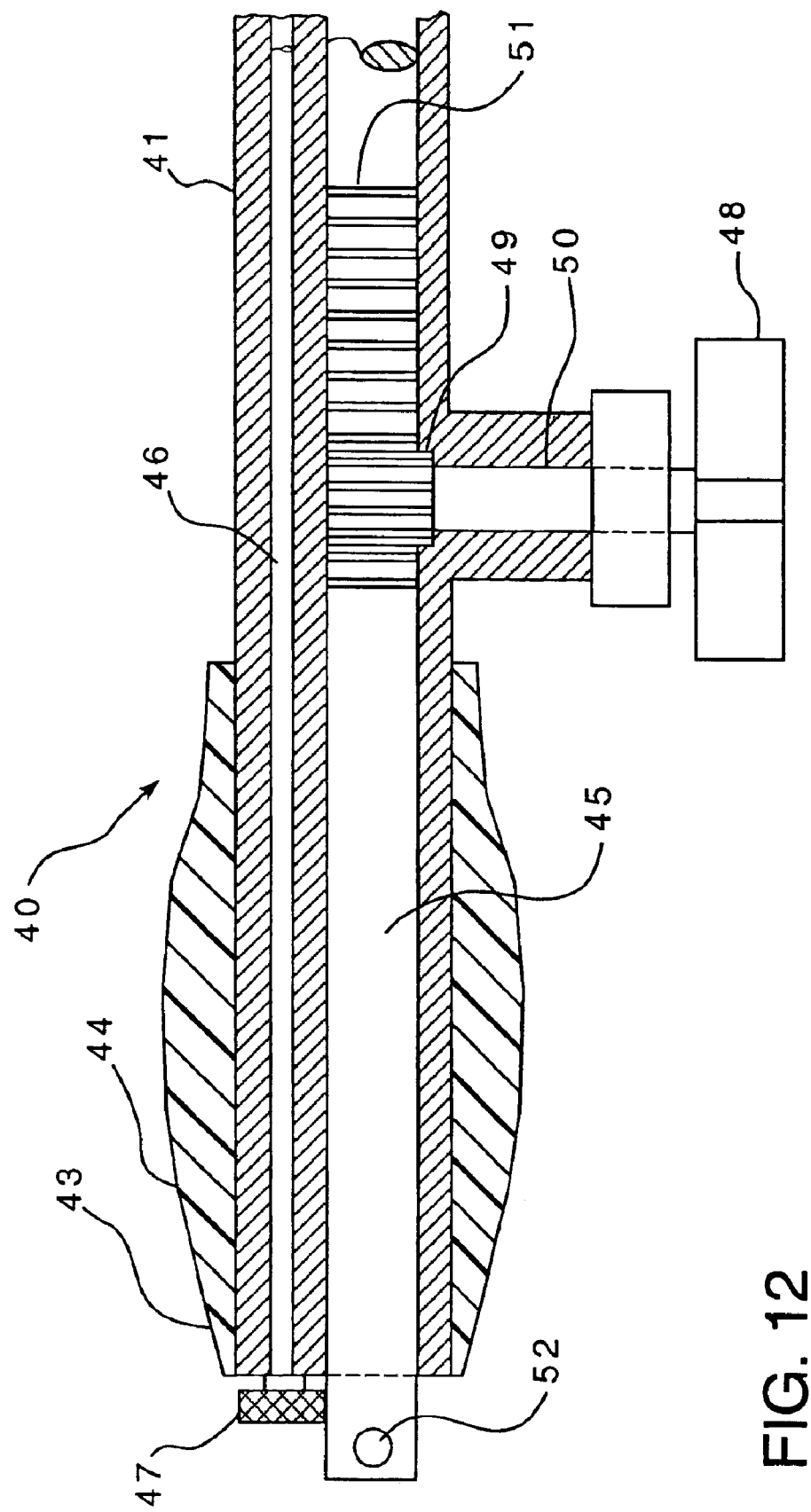
FIG. 12 is a view in side elevation, with major portions shown in vertical mid cross section for exposing the interior, of the proximal end of an elongate insertion tool of the present invention for securement to and manipulation of the full implant plate assembly such as illustrated in FIG. 10.

First portion 11 further includes an elongate arm 18 extending proximally from the first socket element 13. Elongate arm 18 is provided with an elongate through slot 20 therealong. The second portion 12 of assembly 10 comprises a second screw receiving socket element 21 also configured with a screw shank passage 22. Screw shank passage 22 also serves in this instance as a screw head seat to receive the sides of a bone fixation screw head 25 therein with mating intimacy as is illustrated with bone fixation screw 23 in FIG. 11. Second screw receiving socket element 21 is slidably received over arm 18 with its passage 22 centered over and aligned over slot 20 for receiving the shank 24 of a fixation screw 23 therethrough for attachment to an underlying vertebra. Second socket element 12 and slot 20 are configured and dimensioned whereby bottom portions of the screw head 25 (see FIG. 11) seated in the socket element 21 protrude through the second socket element passage 22 and engage edges 26 of slot 20 for clamping the second socket element 21 to arm 18 when screw 23 is fully secured into an underlying vertebra. The edges 26 of slot 20 include a series of adjacent screw head seat depressions 27 for selectively seating portions of the head 25 of bone fixation screw 23. A cap buttress nut 28, illustrated independently in FIGS. 7 through 9, is threadably received in threads 30 of second socket element 21 over the screw head 25 for engaging and covering the screw head. Nut 28 is also provided with bottom protuberances 31 for engaging screw head 25 and thereby closing off the screw head and locking the screw in second screw receiving element 21 in order to prevent accidental backing off or dislodgement of the bone fixation screw 23. In a similar manner, a cap buttress nut 28 is also threadably secured in to first screw receiving socket element 13 for engaging the head of bone fixation screw 17.

Thus second screw receiving element 21 is slidable along arm portion 18 of the first portion 11 of plate assembly 10 with the slot 20 of arm portion 18 underlying the passage 22 for the second bowl 32 for receiving the screw shank 24 of bone fixation screw 23 therethrough and therealong at different desired positions. As previously explained, portions of the head 25 of the fixation screw 23 protrude through the passage 22 for the second bowl 32 of second screw receiving element 21 and seat in one of the depressions 27 to securely clamp the second screw receiving element to the arm portion 18, or thereby to the assembly 10 as a whole when the fixation screw 23 is fully secure into an underlying vertebra. This provides a locking mechanism which prevents further relative movement between elements 13 and 21.

Referring next to FIGS. 12 through 16, the elongate insertion gun or tool 40 of the present invention is illustrated. The insertion tool 40 is releaseably securable to the proximal end 41 of arm 18 of plate assembly 10 whereby the tool 40 and elongate plate assembly 10 extend together end to end in their direction of elongation when secured together, as is best illustrated in FIGS. 13 and 14. Elongate insertion tool 40 is configured for manipulating plate assembly 10 as a whole and also for remotely manipulating screw receiving elements 13 and 21 for adjusting the distance between these elements. The purpose of the insertion tool 40 is to allow the surgeon a convenient tool to hold and control the spinal implant, to provide a mechanism for the minimally invasive placement of the implant, to provide a mechanism by which the spinal implant can be expanded so that it engages previously placed pedicle wires known as K-wires, to provide a mechanism by which the spinal implant may be compressed after placement of the bone fixation or pedicle screws, and further to allow easy release of the implant once the implant is positioned and properly fastened.

The insertion tool 40 has a slender tubular body 41 which tapers to a smaller diameter at its distal end 42 to meet the profile of the plate assembly 10 to which the distal end is attached. This design minimizes the disturbance to the soft tissues during placement of the plate assembly 10. The distal end 42 is curved as illustrated in FIG. 13 to allow the surgeon to easily place and manipulate the spinal implant assembly 10 under fluoroscopy without having the operator's hands at an awkward position. To accommodate this curvature the distal end 42 of the tubular housing 41 is constructed of a material which may be moderately bent to the configuration illustrated and has memory whereby it will retain this selected curvature, as is for example, capable with endoscopes or proctoscopes.

The proximal end 43 (FIG. 12) of insertion tool 40 is provided with a cushioned handle 44. The insertion gun 40 includes two basic longitudinally displaceable rods 45 and 46. Rods 45 and 46 longitudinally slide within tubular housing 41. Rod 46 is slid by manipulating knob 47 and drive rod 45 is longitudinally driven by turning of handle 48 which in turn rotates drive or pinion gear 49 via shaft 50. Drive rod 45 is provided with ring gear rack 51 which completely encircles drive rod 45 and meshes with drive pinion gear 49 whereby when handle 48 is rotated either clockwise or counterclockwise, the drive rod 45 is correspondingly driven either longitudinally to the left or to the right. Thus both drive rods 45 and 46 may be rotated within their tubular housing 41 and are additionally slidably driven longitudinally within tubular housing 41. Drive rod 45 may be rotated by means of bar T-handle 52.

The distal end 55 of drive rod 45 consists of a T-shaped key head which fits into and mates proximal slot 56 in arm portion 18 of plate assembly 10. Locking slot 56 is also provided with an entrance passage 57 whereby the T-shaped locking head 55 when turned vertically presents a narrow profile to slot 57 whereby the distal end 55 of drive rod 45 may be slid proximally and dislodged from the proximal end 41 of plate assembly 10. Second screw receiving element 21 may be manipulated independently of first screw receiving element 13 by sliding movement of drive rod 46. The distal end 58 of drive rod 46 is threadably received into the socket 60 of socket element 21. This treaded engagement may be disengaged by turning knob 47 either clockwise or counterclockwise on the proximal end 43 of the insertion tool 40.

The distal end of first socket receiving element 13, or for that matter of plate assembly 10, includes an open ended guide wire capture slot 61 which communicates with the passage 15 of first bowl 19 of first screw receiving element 13. This is for the capture of K-wire previously implanted in a vertebra for assisting in the guidance and positioning of the plate assembly 10 during the surgical procedure, as will be explained in greater detail hereinafter. In addition, the leading transverse edge 62 of first screw receiving element 13 is provided with a tapered transverse edge which aids in separating soft tissue upon advancing the plate assembly 10 in the body along the spine, and is designed to allow the distal end of the implant to nestle next to the facet joint without impeding the joint's function. This thus may avoid later complications such as arthritis or joint laxity.

The insertion tool 40 allows controlled extension of the collapsed spinal implant assembly 10. The assembly 10 is normally in the collapsed state during implantation as seen in FIG. 14. Once the implant assembly 10 is initially placed by insertion of the insertion tool 40 into the operative site, the positive lock mechanism of key T-head 55 and the positive lock mechanism of threaded proximal end of drive rod 46 in socket 60 is utilized to drive the first screw receiving element forward while the second screw receiving element 21 is maintained in place. This is accomplished by pushing the arm 18 slidably through the second screw receiving element 21 by the drive rod 45, which in turn is accomplished by rotating the handle 48 counterclockwise on the proximal end 43 of the insertion tool 40.

Once the distal first receiving screw element 13 is extended to the proper position and bone fixation screw 17 has been engaged in both screw receiving elements 13 and 21, the surgeon can compress the spinal implant plate assembly 10 by reversing the drive of drive rod 45 and thereby drawing the drive rod 45 back up into the insertion tool 40. Once the implant assembly has been compressed to the surgeon's desired degree, the plate assembly is then locked by driving the proximal screw 23 fully into an underlying depression 27 of arm 18 which thereby clamps screw receiving element 12 to the assembly 10. This locking mechanism holds the spine under compression.

Once this locking maneuver has been accomplished, the cap nuts 28 are engaged in their respective screw receiving elements 13 and 21 and tightened to a predetermined level of torque by a cap nut driver. During this process, the engaged insertion gun 40 is held by the surgeon and allows the implant to be stabilized while acting as an anti-torque device. Once the implant has been secured with the proper amount of torque, the drive rod 45 is disengaged from the implanted plate assembly 10 by turning drive rod 45 90° to the left or the right with the manipulation of handle 52 so that key T-head 55 is positioned vertically and aligned with clearance slot 56 at the proximal end 41 of arm 18. The lock provided by the screw engagement of drive rod 46 with socket 60 of screw receiving element 21 is also threadably disengaged by turning nob 47 counterclockwise at the proximal end 43 of insertion tool 40. At this point the insertion tool 20 is free to be removed from the surgical field.

A detailed of description of the surgical techniques of the present invention are described hereinafter.

SURGICAL TECHNIQUES

The system of the present invention is designed to be inserted with fluoroscopic assistance and therefore the patient, after general anesthesia, is placed on a fluoroscopic compatible OR table in the prone position. The technique described here will be for the L4 and 5 level, but all comments are generally applicable to all spinal levels. The technique described also assumes that a L4/5 PLIF has already been accomplished or inserted in a minimally invasive manner, utilizing an access device such as the Metr-x system (Danek Trademark), although the insertion of the device of the present invention can be accomplished without a prior PLIF as a part of another operation.

With an AP fluoroscopic image, the lumbar spine is imaged with attention to the L4/5 level. The pedicle screw insertion point with this system utilizes the more lateral entry point, described by the intersection of the posterior one third of the transverse process (TP) and the lateral aspect of the facet joint, although other points are also acceptable. This point is ideal, however since the first screw receiving element of the implant assembly 10 has been rounded at its distal end 14 to fit next to the facet joint best if this entry point is utilized. This entry point will allow the implant assembly 10 to nestle next to the upper facet joint without interfering with the joints' movement due to the implants' distal shape, and thus avoids later complications, such as facet pain, laxity or arthritis.

In keeping with this insertion point, a K-wire is laid on the patient's back so that on the X-ray it transects the pedicle of L4 and L5 laterally. The trajectory of the wire is marked on the skin. Subsequently, on the lateral X-ray, the K-wire is laid over the patient so that it points to the L5 pedicle, sloping backwards towards the dorsal lumbar spine at approximately a 45° angle. When this K-wire intercepts the line drawn on the skin, a cross mark is placed and this describes the entry point of the insertion tool 40. Through this insertion point, a T-handled bone needle such as a Jamshade needle is advanced to the insertion point at the L5 level. A K-wire is advanced through the needle and the needle is removed. A stab incision is made at the point of the K-wire insertion and two or three small dilators of increasing diameters are passed over the K-wire to facilitate the passage of the insertion tool 40 with the implant plate assembly 10 secured to the distal end.

As is visualized in FIGS. 17 and 18 at the level of L4/5, a Metr-X access tube 59 is wanded to point at the L4 pedicle. By fluoroscopic image in the AP view, a Bone needle needle is advanced through the Metr-X tube to the insertion point, posterior one third of the TP and the lateral aspect of the facet joint. The Bone needle needle pierces through this bony point and is advanced through the pedicle from lateral to medial and into the vertebral body, care taken not to enter the canal. The stylet of the needle is removed and a K-wire is advanced through the needle and into the L4 vertebral body and the needle removed. See FIG. 19.

Leaving the K-wire in place, the Metr-X access tube is wanded to point towards the L5 pedicle and the exact process that was carried out at L4 is repeated here. The end results are two K-wires protruding from the Metr-X access tube, both marking tapped pedicles.

If the surgeon wishes, a separate cannulated tap can be passed over the K-wires and the pedicles of L4 and L5 are tapped in preparation for screw placement. Note that this tap needs to be an aggressive drill tap to facilitate the minimally invasive placement of the system of the present invention. A better alternative however, would be the use of an aggressive self-tapping cannulated pedicle screw, which eliminates a step in the insertion process and is so illustrated in the drawings.

As is visualized in FIG. 18, at the L5 level, a K-wire sterotaxic guide 63 is slipped over the K-wire 62 and the trajectory of the sterotaxic guide and K-wire is fixed by means of tightening the adjustable arm 64 attached to the sterotaxic guide, thus locking it in place. Leaving the sterotaxic guide 63 in place, the K-wire is removed from the L5 pedicle as is visualized in FIG. 19.

Figure 20:
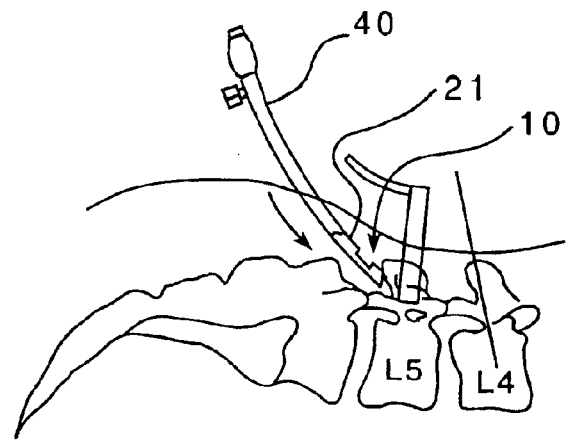
Figure 21:
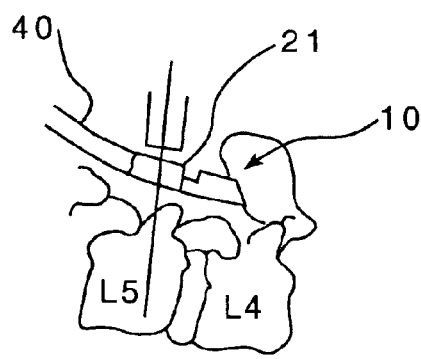
Figure 22:
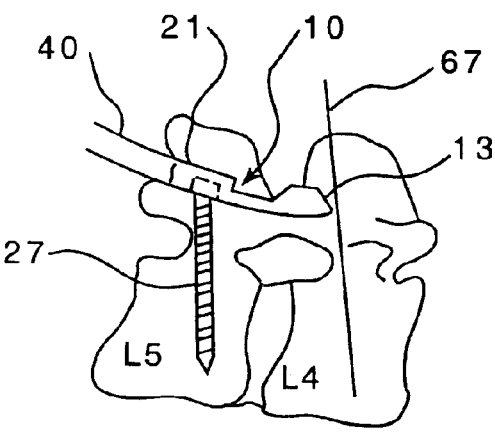

As is next visualized in FIG. 20, the distal end of insertion tool 40 with the implant plate assembly 10 attached is placed through its access channel and advanced under fluoroscopic guidance to align with the L4-L5 pedicle line. The insertion tool 40 is advanced until the second screw receiving element 21 is directly over the L5 pedicle as illustrated in FIG. 21.

This can be confirmed by fluoroscopic view or direct vision via the Metr-X access tube. Once the second screw receiving element 21 is positioned over the L5 pedicle, the K-wire which was removed from the sterotaxic guide is reinserted through the guide, thus capturing the lower screw receiving element as the K-wire continues on into the L5 pedicle. The K-wire is now also passing through the slot 20 in the arm 18 of the first portion of the implant plate assembly 10 as well. The sterotaxic guide 63 is then removed and a self tapping cannulated pedicle screw is driven over the K-wire into the L5 pedicle, but not fully tightened, so only the shaft 24 of the screw 23 extends in the lower screw receiving element 21 and the underlying slot 20.

Figure 23:
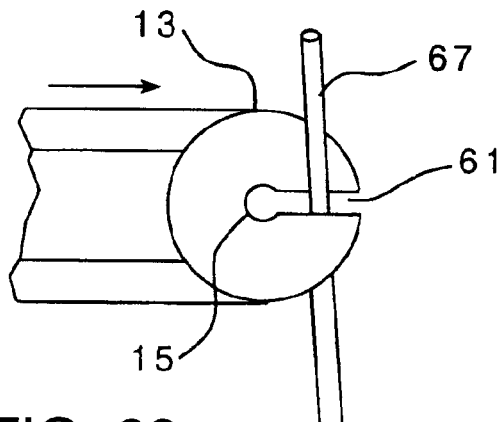

The Metr-X tube is then wanded back towards the L4 pedicle. Using AP fluoroscopy to guide the advance, the rack and pinion drive on the insertion gun 40 is activated by rotating handle 48 counterclockwise and the spinal implant assembly 10 is thereby expanded whereby the first screw receiving element 13 is advanced forward away from the second screw receiving element 21. Fluoroscopy is utilized to aid in engaging the slot 61 at the distal leading edge 14 of the implant plate assembly 10 with the K-wire 67 as schematically illustrated in FIG. 23. Once engaged, so that the K-wire 67 is aligned with the passage 15 of the first screw receiving element 13, a self tapping cannulated pedicle screw is driven over the K-wire 67 and through the passage 15 of first screw receiving element 13 on its way into the L4 pedicle.

Once the first screw receiving element 13 is extended to the proper position and a self tapping cannulated pedicle screw has been engaged and both the first receiving element 13 and the second receiving element 21, the surgeon can compress the spinal implant assembly 10 by reversing the drive of insertion tool 40 by turning handle 48 clockwise and thereby withdrawing the drive rod 45 into the insertion tool 40. This compresses the spinal implant assembly 10 by making the first screw receiving element 13 slide toward the second screw receiving element 21. Once the implant assembly 10 is compressed to the surgeon's desire, the proximal cannulated screw 23 is fully advanced into the second screw receiving element 21 and slot 20 of arm portion 18, thus locking the plate assembly in that position. Since the plate assembly 10 is in the compressed position, the spine is held under compression.

Then two cap nuts 28 are respectively placed over the K-wires and tightened in their respective screw receiving elements 21 and 13 with an appropriate cap nut driver which fits into the hex shaped opening in the top of the cap nut. The driver is turned until a predetermined level of torque is reached and the driver automatically releases. During this tightening maneuver, the insertion gun is held by the surgeon to steady the implant and act as an anti-torque device (or handle).

Once this maneuver is accomplished, rotating drive rod 45 with handle 52 90° as previously explained disengages the release mechanism for the drive rod 45. The locking mechanism for drive rod 46 is also engaged by rotating knob 47 of insertion tool 40 counterclockwise to thereby threadably disengage the distal end of 46 from socket 60 on second screw receiving element 21. The insertion tool can then be removed form surgical field. Once complete, the K-wires are removed and the two incisions are closed with sub-cuticular sutures.

The procedure of the present invention can also be carried out without a previous surgical opening in the lumbar spine. In this case, with an AP fluoroscopic image, the lumbar spine is imaged with attention to the L4/5 level. The pedicle screw insertion point with this systems utilizes the more lateral entry point, described by the intersection of the posterior one third of the transverse process (TP) and the lateral aspect of the facet joint, although other points are also acceptable.

In keeping with this intersection point, a K-wire is laid on the patient's back so that on the X-ray it transects the pedicle of L4 and L5 laterally. The trajectory of the wire is marked on the skin. Subsequently, on the lateral X-ray, the K-wire is laid over the patient so that it points to the L5 pedicle, sloping backwards towards the dorsal lumbar spine at approximately a 45° angle. Where this K-wire 70 illustrated in FIG. 24 intersects the line drawn on the skin, a cross mark is placed and this describes the entry point of the insertion tool 40. Through this insertion point a Bone needle needle is advanced to the insertion point at the L5 level. A K-wire 70 is advanced through the needle and the needle is removed. A stab decision is made at the point of the K-wire insertion and two or three small dilators of increasing diameters are passed over the K-wire to facilitate the passage of the distal end of the insertion tool 40.

A second entry point is marked up for the insertion of the L5 pedicle screw. This point is seen on AP fluoroscopy as approximately 1 cm lateral to the 3 o'clock position of the L5 pedicle. This entry point is marked and through this insertion point a Bone needle needle is advanced through the insertion point at the L5 level. The needle is driven through the pedicle to just inside the vertebral body using AP and lateral fluoroscopy. The stylet of the needle is withdrawn and a K-wire 71 is advanced through the needle into the vertebral body. The needle is then removed. A stab incision is made at the point of the K-wire insertion and two or three small dilators of increasing diameters are passed over the K-wire 71 to facilitate the passage of a cannulated pedicle screw. The larger of the cannulas is left in place with the K-wire protruding through its center.

Figure 24:
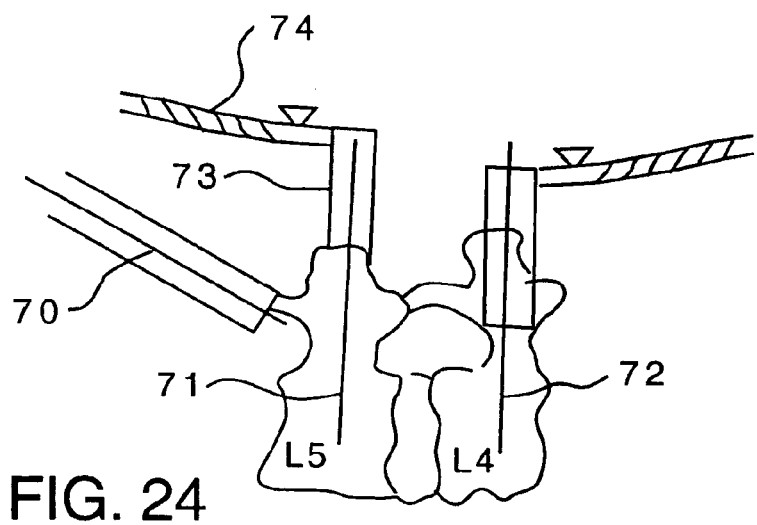
FIGS. 24 and 25 are schematic illustrations of an optional surgical application of the plate assembly of the present invention to the human spine utilizing the insertion tool as illustrated in FIGS. 12 through 16.
Figure 25:
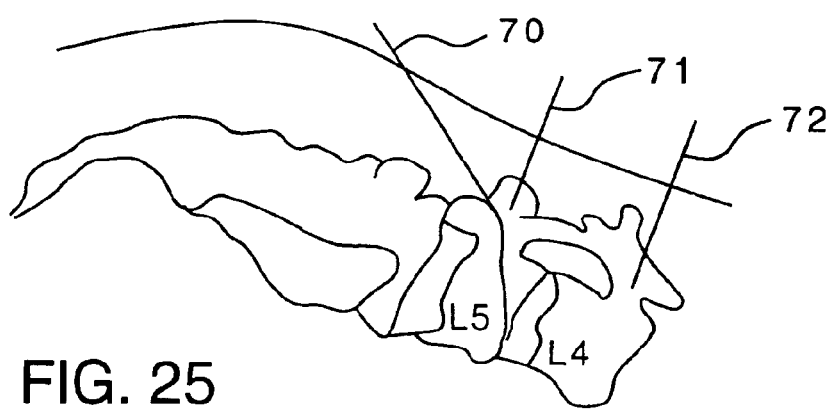

A third entry point is marked out for the insertion of the L4 pedicle screw. This point is seen on AP fluoroscopy as approximately 1 cm lateral to the 5 o'clock position of the L5 pedicle. This entry point is marked and through this insertion point a Bone needle needle is advanced to the insertion point at the L4 level. The needle is driven through the pedicle to adjust inside the vertebral body using AP and lateral fluoroscopy. The stylet of the needle is withdrawn and a K-wire 72 is advanced through the needle into the vertebral body. The needle is then removed. A stab incision is made at the point of the K-wire insertion and two or three small dilators of increasing diameters are passed over the K-wire to facilitate the passage of a cannulated pedicle screw. The larger of the cannulas is left in place with the K-wire protruding through its center as illustrated in FIG. 24. The final placement of the K-wires is illustrated in FIG. 25. The final dilator tube is held in position by an attached adjustable arm designed for this purpose.

Using this technique, the pedicle screws will be projecting slightly inward, through their respective pedicles, which allows the implant assembly 10 to be positioned a bit laterally and away from the facet joints.

At level L5, a K-wire sterotaxic guide 73 is slipped over the K-wire 71 and the trajectory of the sterotaxic guide and the K-wire are fixed by means of tightening the adjustable arm 74 attached to the sterotaxic guide 73, thus locking it in place. Leaving the sterotaxic guide in place, the K-wire 71 is removed from the L5 pedicle. The remainder of the procedure proceeds in an identical manner as when a Metr-X tube is in place as previously described, with the exception that the sterotaxic guide is directed through the lower pedicle dilating cannula, and of course the screws and capped nuts are placed through dilating cannulas as well.

Varing and different embodiments may be made within the scope of the inventive concept herein taught. For example, it may be desirable to surgically repair more than two vertebrae, for example L3, L4 and L5. Accordingly, the implant 10 of the present invention can be configured to have an extra slidable proximal screw receiving element 12 for a total of two proximal bowls 22. In this manner, the implant 10 can be configured to be secured to all three vertebrae and adjusted as described. In this case, the surgical technique is slightly altered since the middle proximal screw receiving element 12 needs to be centered over the central vertebrae to be fixed (L4 in this example) with the insertion tool 40, and the bowl of this central screw receiving element 12 is captured by a K-wire advanced through a preset sterotaxic holder positioned in a manner identical as previously described for the first proximal screw receiving element 12. The implant 10 is then expanded as the insertion tool 40 is withdrawn to allow the most proximal screw receiving element 13 to align with the lowest vertebrae (L5 in this example) and the bowl of the most proximal screw receiving element 12 is then captured by another K-wire via a second sterotaxic holder. Once the two screw receiving elements 12 are captured the device is then expanded forward to capture the last most distal K-wire in the usual fashion via the leading edge slot 61. With this method, more than one level (two vertebrae) can be surgically fixed, which is not possible with present day minimally invasive systems on the market.

It should also be kept in mind that the system of the present invention is applicable to lordotic, kyphotic and straight implant arrangements. Also, the apparatus and system of the present invention can be used both in the thoracic and lumbar spines.

I claim:

1. An implant plate assembly for stabilization of the spine, comprising:
   a first screw receiving socket element at a distal end of said assembly and configured with a screw shank passage and a screw head seat for attachment to a vertebra with the aid of a bone fixation screw;
   an elongate arm extending proximally from said first socket element and having an elongate through slot therealong, said slot having edges, and a series of adjacent screw head seat depressions for selectively seating portions of the head of a bone fixation screw;
   a second screw receiving socket element also configured with a screw shank passage and a screw head seat, and slidably received over said arm with its passage aligned over said slot for receiving the shank of a fixation screw therethrough for attachment to a vertebra;
   said second socket element and said slot configured and dimensioned whereby portions of a screw head of a fixation screw seated in said second socket element protrude through said second socket element passage and engage edges of said slot for clamping said second socket element to said arm when said screw is fully secured in a vertebra.

2. The implant plate assembly of claim 1, further comprising a cap buttress nut threadably received in said second socket element over said screw head for engaging said screw head.

3. The implant plate assembly of claim 2, said nut having bottom protuberances for engaging said screw head.

4. An implant for stabilization of the spine, comprising:
   an elongate implant plate assembly having distal and proximal ends configured for respective attachment to first and second spaced vertebra with the aid of bone fixation screws;
   said plate assembly including first and second screw receiving elements slidably received with respect to each other for adjustably changing the distance between said elements;
   a lock assembly for selectively locking said first and second elements from further relative movement therebetween; and
   said first and second screw receiving elements each having a screw head socket bowl for receiving the head of a bone fixation screw with mating intimacy and a passage in the bottom of each bowl for passage of the shank of a bone fixation screw;
   said second screw receiving element slidable along an arm portion of said plate assembly, said lock assembly including a slot in said arm portion underlying said passage for said second bowl for receiving the shank of a fixation screw therethrough and therealong at desired positions, and said passage for said second bowl and said slot configured and dimensioned whereby portions of the head of a fixation screw received in said second bowl protrude through said passage for said second bowl to engage edges of said slot and thereby clamp said second screw receiving element to said plate assembly when said fixation screw is fully secured to a vertebra;
   wherein said distal end of said elongate implant date has an open ended guide wire capture slot which communicates with said first bowl passage.

5. The implant of claim 4, including locking caps configured and dimensioned for closing off said bowls with bone fixation screw heads seated in said bowls.

6. The implant of claim 5, said locking caps threadably received in said bowls and having bottom protuberances for engaging said screw heads.

7. The implant of claim 4, wherein said distal end has a leading transverse edge which is tapered.

8. The implant of claim 4, wherein said plate assembly is longitudinally curved to mate a specific lordotic curve.

9. The implant of claim 4, wherein said slot is dimensioned and contoured for seating portions of the head of a bone fixation screw protruding from said second bowl.

10. The implant of claim 9, wherein edges of said slot include an aligned series of adjacent screw head seat depressions for selectively seating portions of the head of a bone fixation screw at different positions along said slot.

* * * * *